United States Patent [19]
Zipf

[11] Patent Number: 5,206,594
[45] Date of Patent: Apr. 27, 1993

[54] APPARATUS AND PROCESS FOR IMPROVED PHOTOIONIZATION AND DETECTION

[75] Inventor: Edward C. Zipf, Pittsburgh, Pa.

[73] Assignee: Mine Safety Appliances Company, Pittsburgh, Pa.

[21] Appl. No.: 522,191

[22] Filed: May 11, 1990

[51] Int. Cl.$^5$ ............................................. G01N 27/62
[52] U.S. Cl. ................................. 324/464; 324/459; 250/423 P
[58] Field of Search ............... 324/459, 464, 467, 468, 324/470; 73/23.24, 23.2, 23.22, 23.27, 23.4; 250/424 P, 423 R, 379

[56] References Cited

U.S. PATENT DOCUMENTS

| | | | |
|---|---|---|---|
| 4,013,913 | 3/1977 | Driscoll et al. | 250/423 P X |
| 4,413,185 | 11/1983 | Leveson et al. | 250/423 P |
| 4,476,392 | 10/1984 | Young | 250/423 P X |
| 4,804,846 | 2/1989 | Hall | 324/465 X |
| 4,837,440 | 6/1989 | Burtscher et al. | 324/464 X |

*Primary Examiner*—Jack B. Harvey
*Attorney, Agent, or Firm*—Reed Smith Shaw & McClay

[57] ABSTRACT

Molecular ionization detection and analysis including processes and apparatus for photoionizing trace constituents in a carrier gas or effluent from a chromatograph in a manner that substantially increases the effective sensitivity. The invention uses a pulsed gas valve to introduce a high density gas sample into a vacuum system where the trace constituents in the jet are photoionized by an intense vacuum ultraviolet [VUV] pulse from a flashlamp. The ions are extracted from the beam under free molecular flow conditions. This source may be used with the ion energy analyzer to eliminate any interference due to background gases in the vacuum system and to provide mass analysis of the eluting trace constituents.

27 Claims, 6 Drawing Sheets

CHROMATOGRAPHY PHOTOIONIZATION DETECTOR
HIGH SENSITIVITY MODE: Matched neutral and photon beams

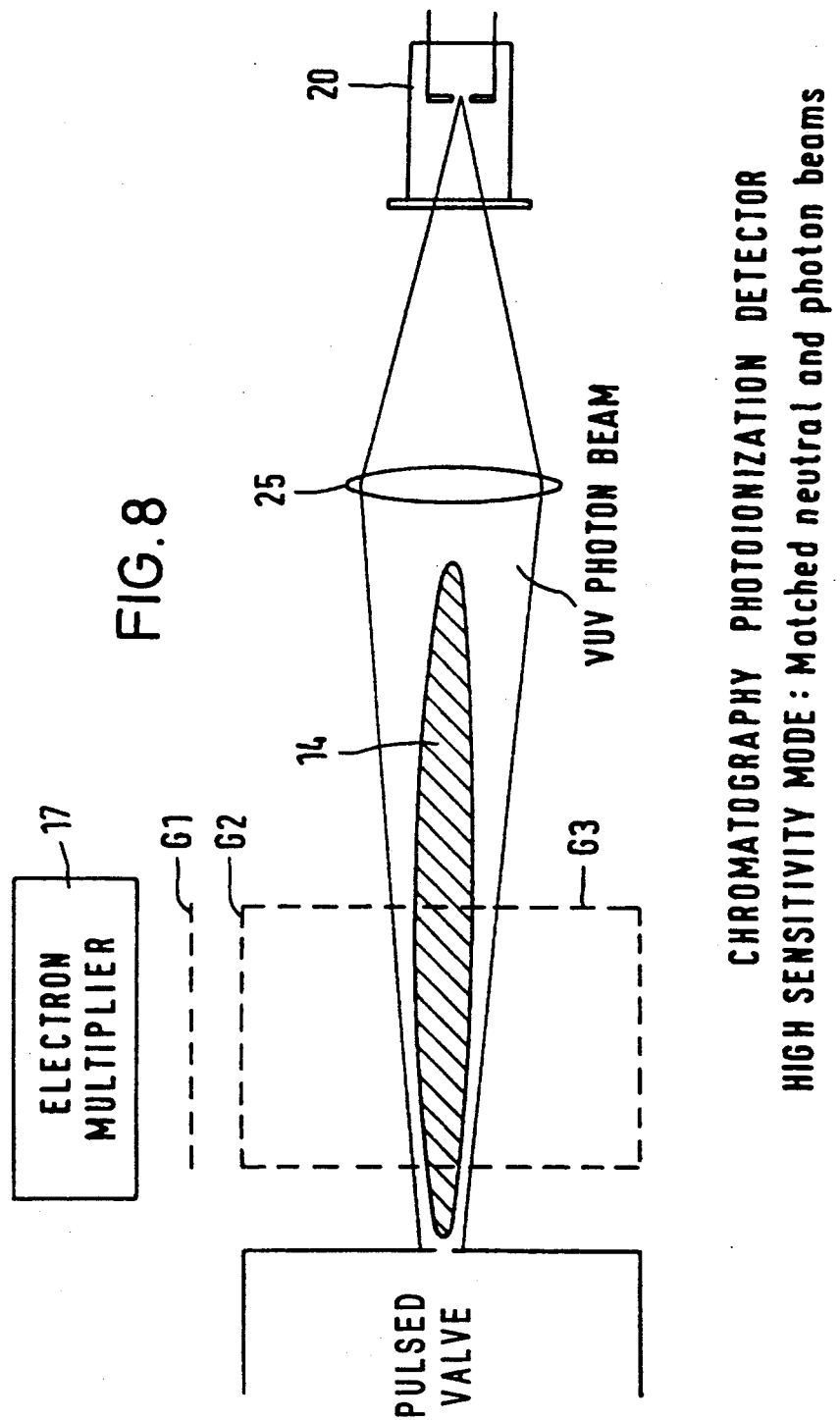

APPARATUS AND PROCESS FOR IMPROVED PHOTOIONIZATION AND DETECTION

FIELD OF THE INVENTION

The invention relates to an improved method and apparatus for photoionization of gases and, in particular, to improved ultraviolet photoionization detection methods and apparatus.

BACKGROUND OF THE INVENTION

It is well known that the photoionization of gases eluting from a chromatograph or leaked into a mass spectrometer provides a useful technique for detecting atomic and molecular species. Although a mass spectrometer is a sensitive analyzer, effective sensitivity is practically limited by a number of processes, including interfering background signals arising from the vacuum system outgassing, the complexities of the fractionation patterns occurring on complex mixtures of high mass number species and the collection of undifferentiated signals due to the detection of metastable species and ultraviolet photons.

The prior art includes a number of techniques designed specifically to reduce background interference. Examples of these techniques are: (1) molecular beam strategies, e.g., U.S. Pat. No. 3,974,380, (2) pulsed input sources, e.g., U.S. Pat. No. 4,365,167 and U.S. Pat. No. 4,855,594, (3) cryogenic techniques, e.g., U.S. Pat. No. 4,039,828, and (4) phase sensitive detection methods, e.g., U.S. Pat. No. 4,258,257 and U.S. Pat. No. 4,263,507. See also U.S. Pat. No. 4,855,594 which utilizes a high density gas sample pulse to sweep residual background from the path of the pulse. However, this method is effective only to about 0.1 ppm.

The ionizers used in these inventions create complex ion fragmentation spectra that often makes it difficult to identify the parent species. This is a significant limitation that compromises the ability of prior-art mass spectrometers to analyze complex organic compounds and biochemical specimens.

The sensitivity of prior art photoionization detectors is further limited in that they cannot detect single ions or very small concentrations of ions. This limitation is due to the fact that these detectors use simple electrodes or Faraday cups to collect the ions and operate at essentially atmospheric pressure; thus, precluding the use of charge-particle multiplier devices which require pressures of less than $10^{-4}$ torr. In general, the local ion density in the detectors belonging to the prior art must exceed $10^5$ ions/cm$^3$ in order to be detected by conventional electrometers in the presence of the shot noise background.

Accordingly, it is an object of the present invention to provide new methods and apparatus for substantially increasing the sensitivity of mass spectrometers and gas chromatographic detectors. It is a further objective of the invention to provide a new photoionization method for vacuum ultraviolet flux irradiation of gas samples.

SUMMARY OF THE INVENTION

Generally, the present invention provides a method for selectively photoionizing a sample gas by introducing the gas as a high density stream at a pressure from about 0.8 to 150 Torr into a spatially limited ionization region of a vacuum chamber and directing a flash of high intensity vacuum ultraviolet photons at the gas as it enters the ionization region. The vacuum chamber is maintained at pressure of less than $10^{-3}$ Torr. In a preferred embodiment of the invention, the gas is introduced as a pulse with a particle density greater than $2(10)^{16}$ (atoms/molecule) cm$^{-3}$.

The invention also provides methods and apparatus for collecting selected ions from the ionized gas and detecting the collected ions. For example, in one embodiment an ion collection means is provided that does not discriminate against background interference. In this embodiment, a vacuum ultraviolet [VUV] flash lamp is preferably used with a lens, such as a magnesium fluoride lens or mirror to focus a high-intensity image at the intersection or parallel to the direction of an expanding neutral particle beam.

The photo-ions produced at the intersection region are collected and focused by a pair of cylindrical grids and a planar grid. The collected and transmitted ions are then detected by an electron multiplier.

In a preferred embodiment of the invention, the expanding neutral beam has a particle density $>2(10)^{16}$ (atoms-molecules)·cm$^{-3}$ and preferably $>5.5(10)^{18}$ (atoms-molecules)·cm$^{-3}$ at the intersection of the expanding beam and the high intensity photon flux. This beam density and geometry has the advantage of overcoming ion mobility and ion chemistry limitations typically associated with prior art photoionization techniques. A coaxial electrostatic analyzer located along the axis of the beam assists in reducing space charges.

In another preferred embodiment of the invention, a pulsed valve is used to introduce a high-density gas sample into a vacuum chamber where the molecules are ionized by VUV photons. By focusing the high intensity photons into an area substantially the same as the cross-sectional area of the expanding gas beam, an extremely efficient photoionizer is provided.

In the present invention, ions are produced in a region of a relatively high density neutral beam which is spatially limited and collected by an ion energy analyzer which reduces space charge effects and selects ions in a limited kinetic energy range. In addition, an aperture is placed along the axis of beam which stops and deflects the beam. In this manner, ions are collected behind the aperture and focused. The background signals are substantially reduced or eliminated because the kinetic energy of the background ions is less than the energy of the ions from the ionizer and unwanted photons and excited neutral and ion species are physically prevented from reaching the detection region. Accordingly, since ions of different masses arrive at the detector at different times, the detector can select only the ions having the correct energy and transit time characteristics.

In another embodiment the photoionizer is provided with an aperture stop to effectively discriminate against the background as well as any dissociation fragments. The ions and the neutral gas jet enter the ion energy analyzer which is preferably a strongly focused double electrostatic lens with a high energy resolution, for example $\Delta E/E \sim 0.01$ at 10ev. Consequently, the present invention rejects all fragments (normally created by prior art photoionization methods) and accepts only the parent ion.

The photoionizer of the present invention is useful in a number of applications. In particular the photoionizer may be used in mass spectrometry as well as gas chromatography. Because the ionizer operates at a very high pressure and uses a strongly focussed double Einsel lens, the ion analyzer can minimize space charge effects while measuring the ion energy and transit time of the large positive ion pulse. Using a pulse jet valve or nozzle, the velocity of the gas through the throat provides kinetic energy to the entrained molecules. However, the added kinetic energy is not so high as to produce the dissociation of molecules. These ions can be analyzed (time and energy) as a mass spectrometer taking advantage of the narrow forward velocity of the ions and various electrostatic lenses.

In other applications of the invention, the ionizer is connected to the outlet of a chromatograph to analyze the gases eluting therefrom. The output of the chromatograph column is connected to the pulse valve so that the effluent is injected into the vacuum chamber. Preferably, the pressure at the pulse valve is about 0.1 to about one atmosphere. The ions are extracted at a flow velocity of about $3(10)^5$ cm sec$^{-1}$. By means of this method, the signal to noise ratio is considerably enhanced and it is possible to detect a single ion. To improve resolution, electrostatic lenses can be utilized.

Other advantages of the present invention will become apparent from a perusal of the following detailed description of presently preferred embodiments taken in connection with accompanying drawings.

BRIEF DESCRIPTION OF THE DRAWINGS

FIG. 8 is schematic view of the present invention in which the VUV flash lamp is focussed on the expanding gas beam along its axis.

DETAILED DESCRIPTION OF THE INVENTION

Figure 1:
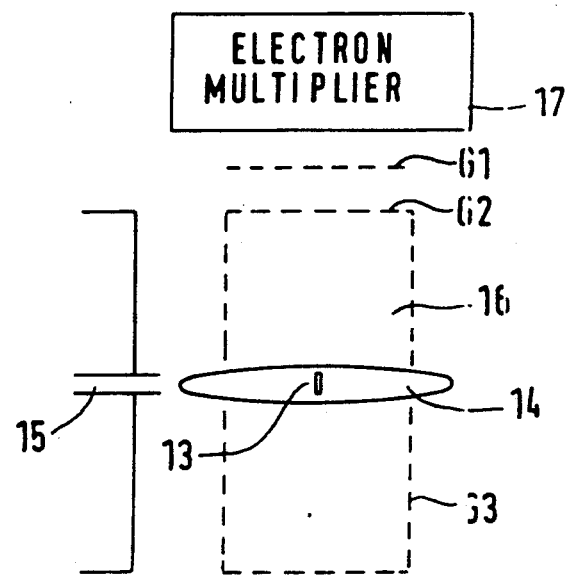
FIG. 1 is schematic diagram of the photoionizer of the present invention utilizing an ion collection means that does not discriminate against background interference.

Referring to FIG. 1, an image 13 of a VUV flashlamp (not shown) is depicted at its intersection with expanding neutral beam 14. The photons from the flashlamp intersect at an axis perpendicular to the axis of the neutral beam 14. Preferably, the VUV flashlamp is a EG & G, type XFA-504. Neutral beam 14 is produced by nozzle 15 preferably a pulse nozzle which injects a standard carrier gas such as argon, helium or the like, into a vacuum chamber 16. Chamber 16 is at a pressure less than $10^{-3}$ Torr atmospheres, and preferably less than $10^{-4}$ Torr. The density of beam 14 is preferably in the range of greater than $2(10)^{16}$ (atoms/molecules)·cm$^{-3}$ to greater than $5.5(10)^{18}$ (atoms/molecules) cm$^{-3}$. The pulse nozzle is preferably one made by J. M. Jordan Company/or equivalent which creates high density pulses at a rate of about 10 pulses/sec.; higher rates are feasible using piezoelectric valves.

The photo-ions produced at the intersection are collected by cylindrical grids G2 and G3 which have a potential difference of 5 volts and 15 volts, respectively, with respect to the common circuit. These grids are positioned as close as possible to the outlet of pulse nozzle 15. With the Jordan valve this is about 5 mm. The ions are detected by charged particle multiplier 17 after passing through planar grid G1. Grid G1 functions as an electrostatic shield to prevent the electric fields created by the multiplier from penetrating into the ionization region and is normally held at ground potential. Multiplier 17 may be a Johnston Laboratory type MM-1 multiplier which can be operated in either a current detection mode (amplified electrometer) or as a single ion detector. Preferably, the particle multiplier, is positioned from 1 to 5 mean free paths from the ionization region; more preferably 1 mean free path.

The ion collection means described in connection with FIG. 1 does not discriminate against background interference. However, the means shown with respect to FIG. 2 can be configured to provide background discrimination.

Figure 2:
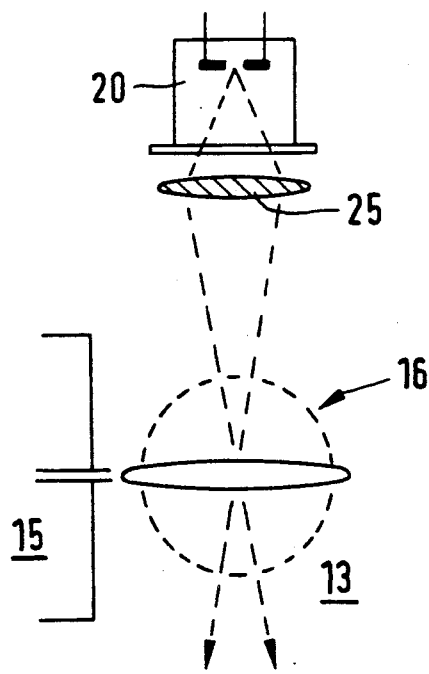
FIG. 2 is a schematic diagram of the present invention showing the use of a VUV flashlamp and lens to focus a high-intensity VUV image on an expanding neutral beam.

Referring to FIG. 2, a VUV flashlamp 20 and magnesium fluoride lens 25 are shown. Instead of a lens, other focusing means, such as a mirror may be used to focus the photons into the desired region. Lens 25 is used to focus a high-intensity VUV image on expanding neutral beam 14 which has a particle density $>2 \times 10^{16}$ cm$^{-3}$ at the position of the incident VUV beam. Grids G1, G2, and G3 are shown as viewed from the top.

The VUV arc image 13 can be made as small as 1.5 mm × 0.1 mm, while the VUV pulse has a duration from about 0.1 to 3.0 μsec to as little as 300 ns full width half maxima FWHM or less than 100 ns for the windowless flashlamp.

FIGS. 1 and 2, thus show the essential features of the present invention. The invention requires the use of a small vacuum chamber 16 which is evacuated by a trapped forepump. More elaborate pumping systems can be used if the ions created by this invention need to be amplified by a charge-particle multiplier or analyzed by a mass spectrometer. A pulsed valve 15 as described hereinabove is used to introduce a high-density gas sample obtained directly from the GC column or other source into vacuum chamber 16.

The mixing ratio of a trace constituent in the supersonic or subsonic jet 14 issuing from pulsed valve 15 is essentially the same in magnitude as its relative density in the carrier gas. If the flow velocity of the gas pulse is $v_p$, the kinetic energy of the trace constitute is given by $KE = mv_p^2/2$, where m is the mass of the species. It is important to note that the kinetic energy of the trace constituent is at least an order of magnitude larger than that of any background molecule or atoms of the same molecular (atomic) weight that may be in the chamber as an outgassing product, residual from previous pulses or backstreaming from the pumping system.

This difference in kinetic energy is used to eliminate interference from the background gas. This approach also permits the use of more limited and less expensive vacuum pumping equipment (forepump) rather than turbo molecular, cryogenic, or diffusion pumps when the detector is operated in the preferred embodiment.

Molecules in the sample gas pulse are ionized by a pulsed flux of vacuum ultraviolet photons 13 produced by a flashlamp or laser 20. The preferred VUV flashlamp used in this invention can deliver at least $10^{11}$ to as many as $10^{17}$ VUV photons in a pulse that has a FWHM as short as 0.3 μsec or less. This beam of photons is focused into a small rectangular image 13 (1.5 mm × 0.1 mm) that is matched to the dimensions of the expanding jet by a magnesium fluoride lens 25. This geometry results in a photoionizer with exceptional efficiency, that yields a narrow (time and spatial) ion pulse (see FIG. 3), and that is ideal for analysis by a time-of-flight mass spectrometer.

The system noise corresponds to a minimum detectable signal of much less than 1 pptv in the preferred embodiment.

(A) Total Ion Mode (Faraday Cup Collection)

FIGS. 1 and 2 illustrates the simplest detection means. The photoionization region is surrounded by a cylindrical grid G3 that is biased positively. The newly formed photo-ions are focused by this lens and grid G2 towards G1 under free molecular flow conditions (not mobility limited). An extraction ion velocity approaching $10^6$ cm/sec or greater can be achieved easily by applying potential to the grid structure in a practical range of 5 to 15 volts.

Figure 3:
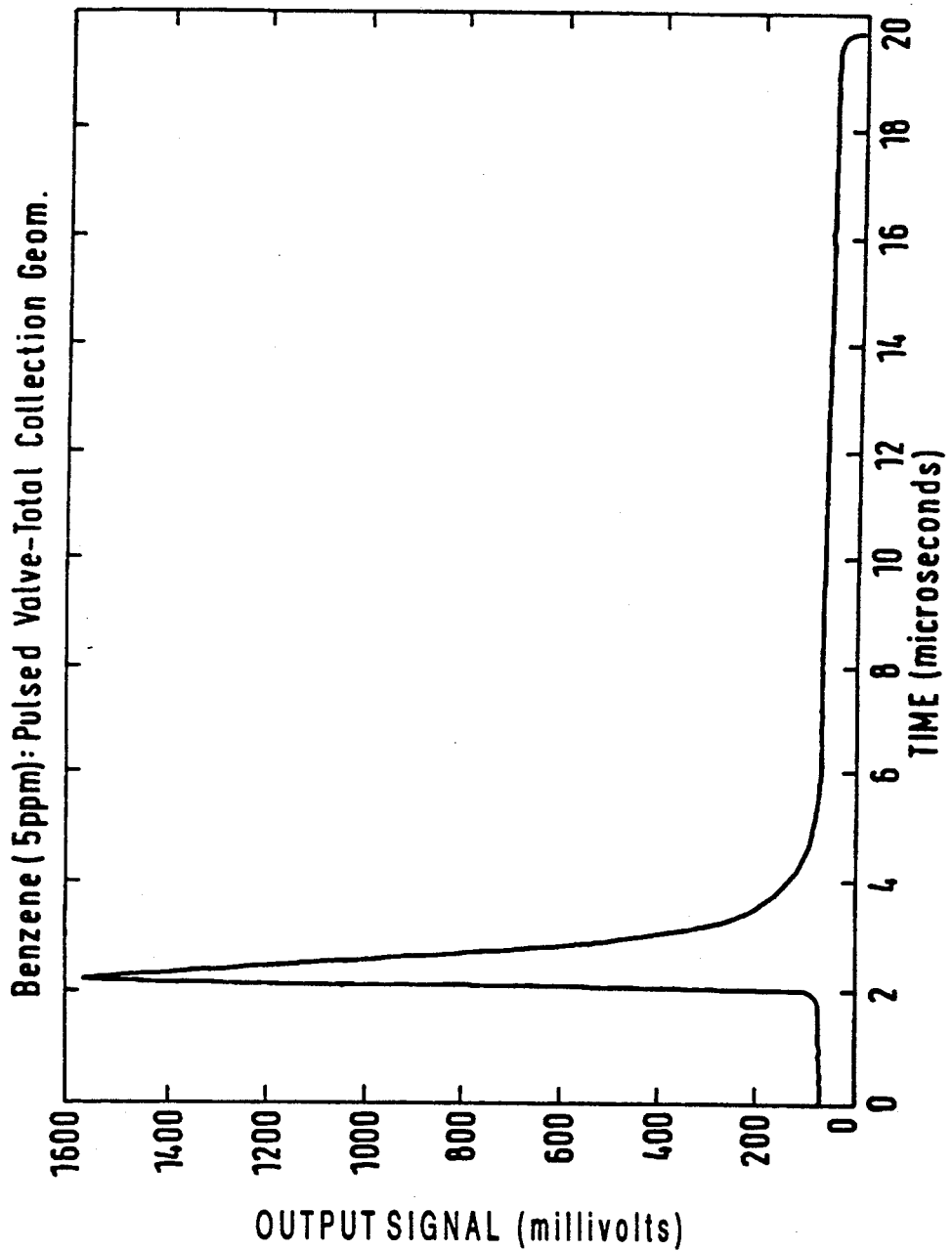
FIG. 3 a graphical illustration of the detection of benzene at a concentration of 5 ppmv in nitrogen using electrometer-mode detection.

FIG. 3 shows the detection of benzene by the preferred means at a concentration of 5 ppm under conditions where the system noise level is at least seven orders lower than the prior art. The very large gain in effective signal-to-noise is achieved because the ions can be extracted from the expanding jet in submicrosecond times thereby producing a very large signal in the supporting sample-hold electronics whose very narrow gate strongly discriminates against random system noise. This detection technique does not directly discriminate against the production of photo-ions from the residual gas. For the sample system illustrated, the use of higher-pumping speed vacuum equipment (e.g., turbo molecular or cryogenic pumps) which will reduce the background gas pressure, will improve the achievable signal-to-noise ratios even more.

Figure 4:
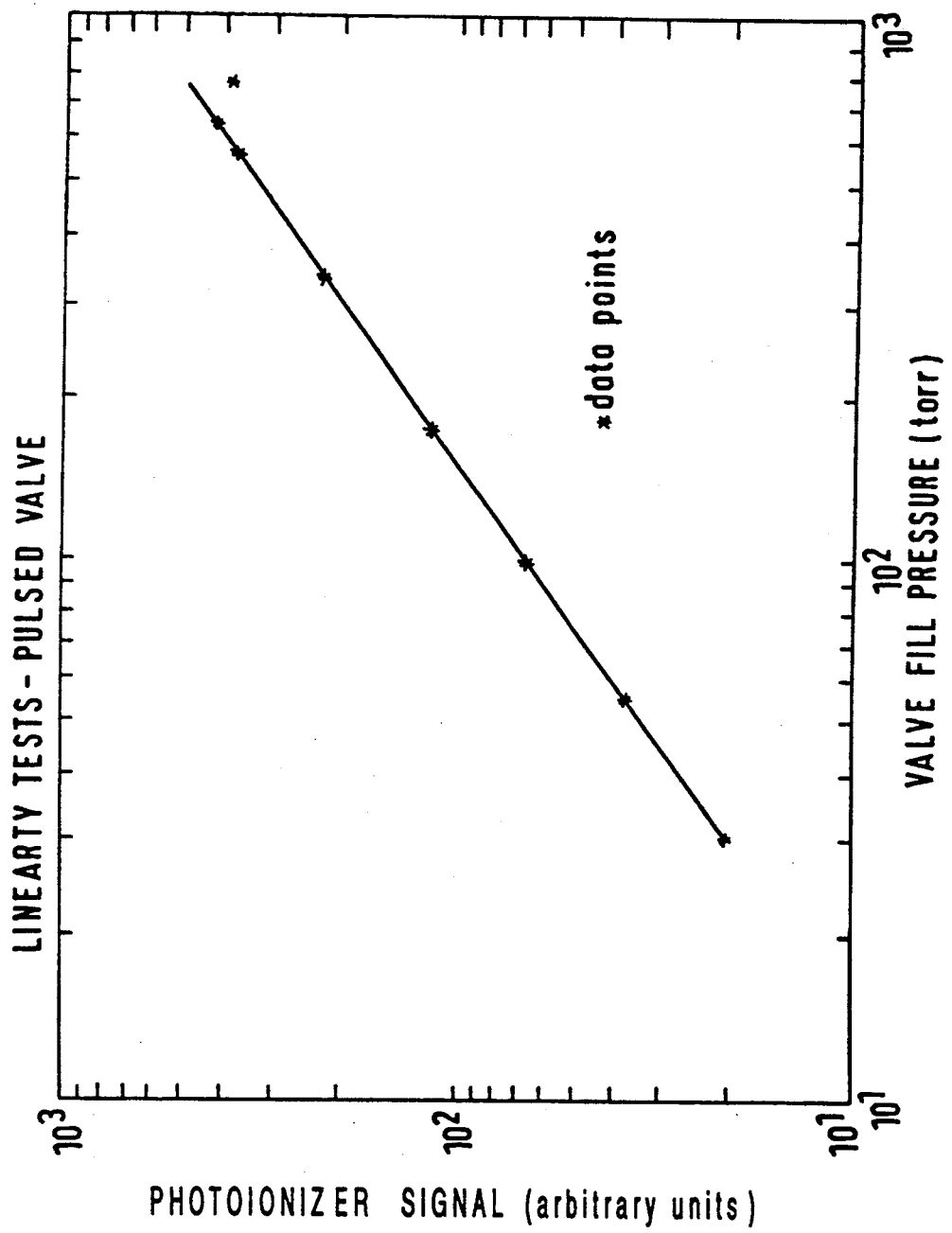
FIG. 4 graphically illustrates the linearity of the pulsed photoionization detector versus the head pressure in a pulsed valve.
Figure 5:
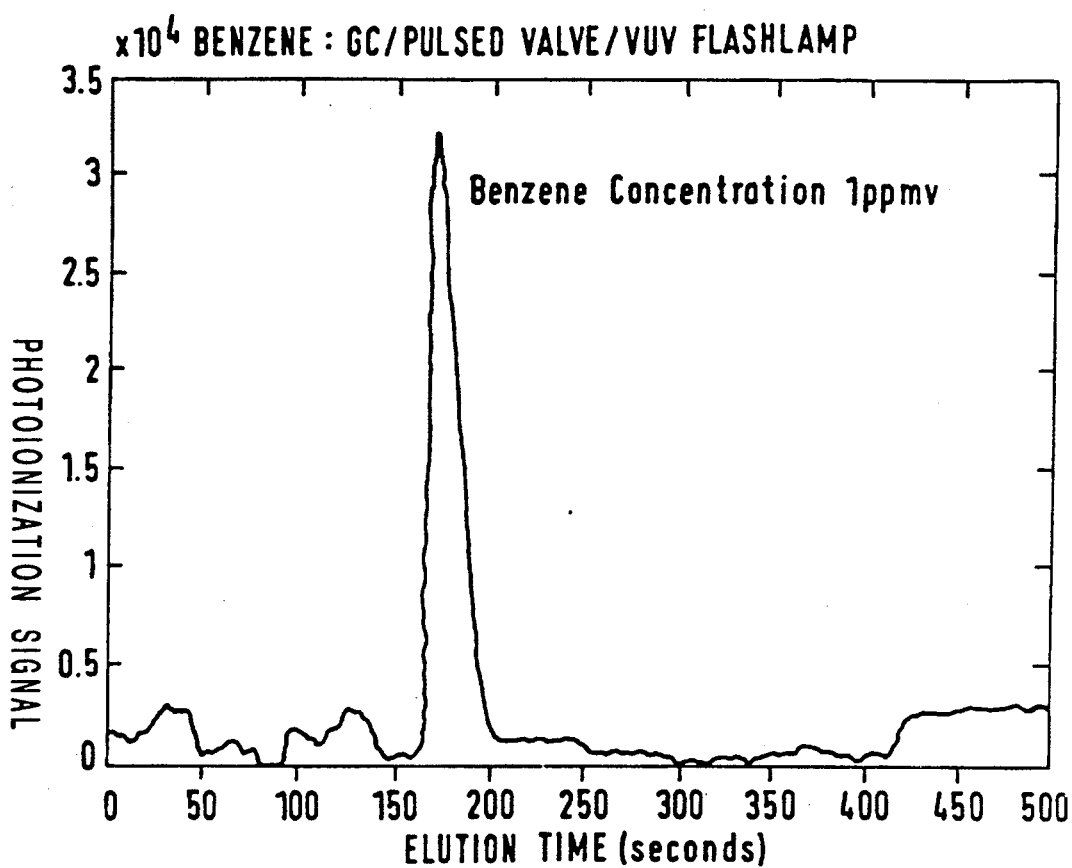
FIG. 5 is a gas chromatogram showing the detection of benzene using the pulsed photoionizer described in this invention.

The data shown in FIG. 3 were obtained in electrometer operation mode with electron multiplier 17 used simply to amplify the ion pulse. A gain of 11 was used to obtain these results. Electron multiplier 17 can be operated at a gain of $10^7$ if necessary, so much greater sensitivities are readily achievable in the preferred embodiment, if needed. The excellent linearity of detector 17 is illustrated in FIG. 4 while a representative gas chromatogram obtained by using this detector is shown in FIG. 5.

The detection system can also be operated in a pulse-counting mode in which single ions are detected separately and counted. This feature gives the invention a sensitivity at least five order of magnitude greater than photoionization detectors described in the prior art, and it facilitates the use of digital data processing techniques for noise suppression and signal enhancement and retrieval.

(B) Total Ion Mode (Positive Discrimination Against Residual Background Gases And Dissociative Ionization Fragments)

Figure 6:
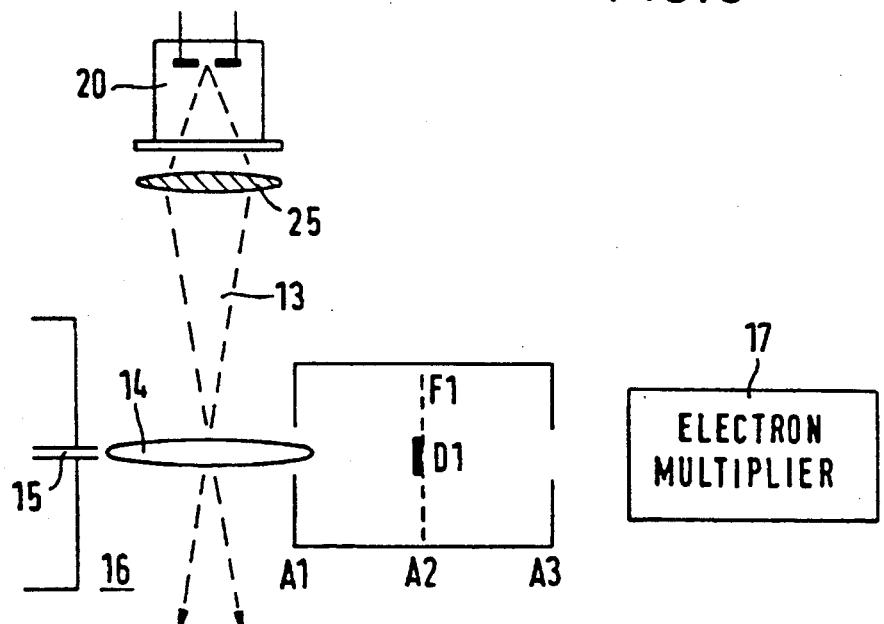
FIG. 6 is a schematic illustration of the present invention which eliminates interference from background ions or debris and mass analyzes the trace constituents in the eluting gas.

FIG. 6 shows the GC photoionization detector which discriminates against residual background gases and dissociative ionization fragments. The principle of the invention is as follows: Molecules in the neutral jet are ionized by a pulsed flux of vacuum ultraviolet photons 13 produced by a flashlamp 20. The ions and the neutral gas jet enter the ion energy analyzer which is a strongly focused double electrostatic lens with an energy resolution that can be as high as 0.1% at 10eV. The electrostatic lens consists of a conducting cylinder A2 that is aligned coaxially in the direction of the effusing jet 14. A1 and A3 are planar lens elements with circular apertures located perpendicular to the axis of the cylindrical structure with a diameter d.

The cylinder has a high transparency grid F1 located at its center. The plane of the grid is perpendicular to the axis of the lens and the jet direction. The grid is made of a conductive high-transparency mesh. A potential, $V_o$, is applied to the cylinder and grid. This positive potential determines the minimum energy that an ion must have in order to pass through the lens structure. The strong focusing properties of the lens provides the dispersion needed to select ions only in the energy range $eV_o \pm \Delta eV_o$. The energy bandwidth, $\Delta eV_o$, is determined by the dimensions of the lens and is given by the formula: $\Delta eV = V_o d / 6D$ where D is the diameter of the cylinder A2, and d is the diameter of the exit aperture A3.

A small metallic stop aperture D1, with a specially contoured surface is welded to screen F1 on the geometric axis of the analyzer. The diameter of the contoured stop aperture is chosen so that it intercepts the neutral beam 14, any Rydberg or metastable molecules in beam 14 and any VUV photons produced by the ionizing process and deflects them away from detector 17 or mass spectrometer 17. This innovation over prior art effectively eliminates the principle sources of the undifferentiated ion background that limits the sensitivity of prior art mass spectrometer systems. The cylinder used in the electrostatic lens is constructed from high-transparency wire mesh which allows the particles and photons intercepted by the disc to escape to the walls of vacuum chamber 16 without compromising the performance of the mass spectrometer or detection system.

In normal operation, the minimum transmission energy, $eV_o$, of the ion analyzer is set well above the kinetic energy of any ions formed by the photoionization of the background gases. The dimensions of the ion analyzer are chosen so that the bandwidth of the instrument allows the parent ion to pass through but prevents any ions created by the fragmentation of the parent molecule during the primary photoionization process from reaching the detector. The simultaneous rejection of background and fragmentation ions and the exclusive selection of the parent ions is a unique feature of this photoionization detector that is achieved by very simple measures.

For example, A1 and A3 are planar lens elements with circular apertures having a diameter d located on the axis of the cylindrical analyzer. A2 is a cylindrical lens element with an inner diameter D. Grid F1 is located at the center of A2 and is positioned perpendicular to the axis of the lens. Stop aperture D1 is spot-welded to F1 at its center and prevents the neutral beam from entering the electron multiplier 17 directly by deflecting the neutrals, any excited species in the beam or VUV photons created in the ionizer towards the walls of A2 which may be constructed of mesh material to enhance the rejection of these potentially interfering species. F1, A1 and A3 prevent neutral species and UV photons from multiplier 17.

(C) Time-Of-Flight Mass Spectrometer Mode

The ions formed by the VUV flashlamp 20 which is imaged on the expanding pulsed jet 14 can be made very narrow in both the time and spatial domain. The photo-ion pulse width can be as narrow as 100 ns FWHM or less and can be confined spatially to a width of only 0.1 mm in the direction of the jet velocity 14. The photo-ion-pulse is first processed by the ion energy analyzer which deflects the neutral beam and metastable and Rydberg species and prevents VUV photons from entering the mass spectrometer and detector and eliminates background ions based on energy discriminants. In the time-of-flight [TOF] spectrometer mode, the trace constituent ions then pass into a field-free drift region of a conventional TOF mass spectrometer and will yield a complete mass spectrum for each flash. Alternatively, a magnetic or quadruple mass spectrometer can be used in a mode that scans the mass spectrometer slowly so that many flashes are required to produce a complete mass spectrum. The TOF mass spectrometer option is considerably more efficient because it samples a wide mass range following every VUV flash but generally which has poorer resolution.

(D) Ion-Energy Mass Analysis Mode

Figure 7:
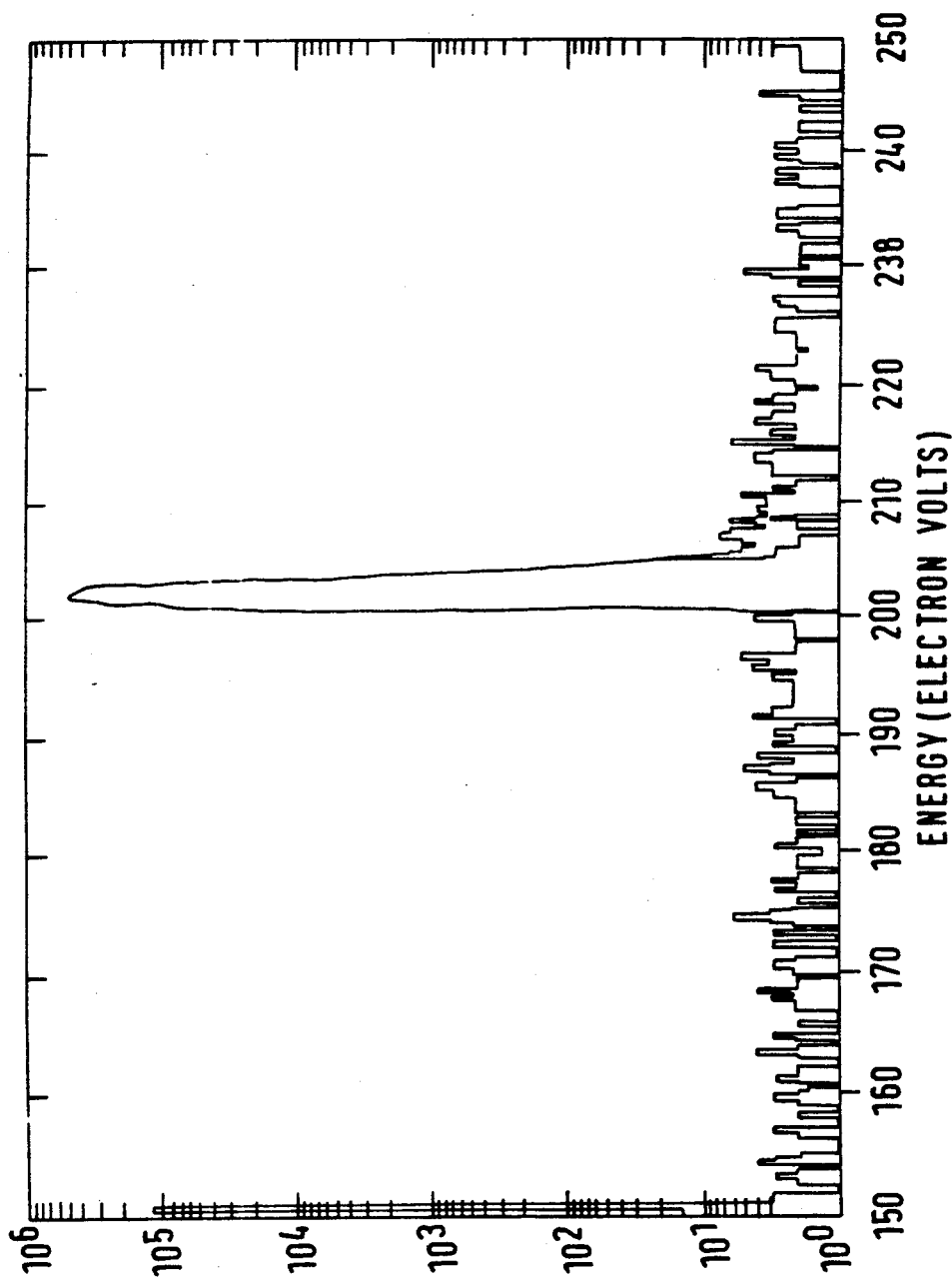
FIG. 7 illustrates the energy resolution of the ion analyzer used in this invention.

The ion energy analyzer described with respect to FIG. 6 generally comprises elements A1, A2, A3, F1, and D1 is used to discriminate against interfering signals from the background gas or from fragment ions produced dissociatively by the basic ionization process. In this embodiment, the ion analyzer is operated with a low resolution ($\Delta E/E \sim 0.1$) and a very sharp lower energy limit that achieves discrimination very well, namely, eliminating the background and fragment ions while allowing all parent ions to pass through. In the Ion-Energy (IE) Mass Analysis mode, the ion analyzer is operated with high resolution ($\Delta E/E \sim 0.01$) in order to transmit only those ions with kinetic energy in a very narrow range (FIG. 7).

Since the kinetic energy of an ion in the jet 14 depends on the mass of the ion, $K.E. = Mv_p^2$, where $v_p$ is the flow velocity, an energy analysis at high resolution yields the mass spectrum of the photo-ions in the jet. The ion analyzer is in effect a high-efficiency mass spectrometer. The ion analyzer used in this invention has an exceptionally well-defined energy bandpass. This can be seen in FIG. 7 which shows that the shape of the energy window is rectangular with nearly vertical 'walls' extending down for at least six orders of magnitude with no detectable skirts or wings. It should be noticed that the steep skirts define the edges of the energy bandpass and the absence of any 'wings' on the transmission curve. Also noteworthy is the out-of-band rejection factor for this analyzer is greater than $10^7$ to 1.

This characteristic of the ion analyzer permits it to work very effectively even at the low absolute energies of the ions found in the expanding gas jet. The performance of the instrument is also helped by the low kinetic temperature of the gas atoms and molecules entrained in the expanding gas jet reduces the degradation of the instrument's resolution because of diffusion effects. The Ion-Energy mass spectrometer is a very compact instrument, having few parts and does not require any complex alignment procedures or potentials for proper operation, and therefore represents a significant improvement over the prior art.

Finally, FIG. 8 shows the focusing of the VUV photons using $MgF_2$ lens 25. In this case the photons from the flash lamp are directed parallel to the axis of beam 14 in the ionization region to provide high sensitivity geometry. In this embodiment the vacuum ultraviolet (VUV) photons created between the electrodes of the flashlamp are collected and collimated into a converging beam by a magnesium fluoride lens 25. The beam of VUV photons is focussed on the exit orifice of the pulsed valve 15 and is positioned on the axis of the valve so that the incoming VUV beam intersects the neutral beam effusing from the valve in a matched fashion. This arrangement maximizes the formation of photoions in the collection region defined by the grid structure consisting of the elements G1, G2, and G3. The collected ions are detected by the electron-multiplier or Faraday cup located at position 17. This VUV beam/valve geometry is nearly two orders of magnitude more sensitive than the high time-resolution detector shown in FIG. 1.

While presently preferred embodiments of the invention have been shown and described in particularly, it may be otherwise embodied within the scope of the appended claims.

What is claimed is:

1. A method for selectively photoionizing a sample gas comprising the steps of:
   A. introducing said gas into a spatially limited ionization region of a vacuum chamber in a high density stream at a pressure of from about 0.8 to 150 torr, said vacuum chamber being maintained at a pressure less than $10^{-3}$ torr; and
   B. directing a flash of high intensity vacuum ultraviolet photons at said gas as it enters said ionization region.

2. A method as set forth in claim 1, wherein said stream is introduced as a pulse.

3. A method as set forth in claim 1, wherein said gas is introduced with a particle density greater than $2(10^{16}$ (atoms/molecules)$\cdot cm^{-3}$.

4. A method as set forth in claim 1, wherein said sample gas includes trace constituents that absorb ultraviolet radiation for ionization.

5. A method as set forth in claim 1, wherein said pressure in the ionization region is from about 0.1 to 1.0 atmosphere.

6. A method as set forth in claim 1, 2, 3, 4 or 5, wherein said sample gas is eluted from a chromatograph.

7. A method for selectively photoionizing and detecting a constituent of a gas sample comprising:
   A. introducing said gas into a vacuum chamber in a high density stream at a local pressure of from 0.8 to 150 torr;
   B. directing a flash of high intensity vacuum ultraviolet photons at said gas as it enters said vacuum chamber, to ionize said gas in a spatially limited ionization region;
   C. collecting selected ions from said ionization region; and
   D. detecting said collected ions external of said ionization region.

8. A method as set forth in claim 7, wherein said collected ion is a single ion.

9. A method as set forth in claim 1 or 7, wherein said vacuum ultraviolet photons are flashed for between 0.1 and 3.0 $\mu sec$.

10. A method ad set forth in claim 1 or 7, wherein said ultraviolet flash is focused on an area having a cross-sectional area substantially the same as said gas stream.

11. A method as set forth in claim 1 or 7, wherein said ultraviolet flash is focused along the axis of said gas stream in said ionization region.

12. A method as set forth in claim 7, wherein said stream of ionized gas is inhibited from flow along an axis of its introduction.

13. A method as set forth in claim 7, wherein said stream is introduced as a pulse.

14. A method as set forth in claim 7, wherein metastable, UV photons and ionized gas are inhibited from flowing along said axis of introduction.

15. Apparatus for ionizing a sample gas comprising:
A. a vacuum chamber;
B. valve means for introducing at a pressure of 0.8 to 150 torr a stream of said sample gas into said vacuum chamber, said valve being connected to a source of sample gas; and
C. a vacuum ultraviolet (VUV) flashlamp positioned to direct a pulsed beam of VUV photons on to said stream of sample gas within said vacuum chamber.

16. Apparatus as set forth in claim 15, wherein said valve is a pulse valve for introducing said stream in pulses at a predetermined pulse rate.

17. Apparatus as set forth in claim 16, wherein said flashlamp directs at least $10^{11}$ VUV photons per pulse at said pulse rate of the sample gas.

18. Apparatus as set forth in claim 15 including a time of flight means spectrometer.

19. Apparatus for ionizing and detecting a constituent of a sample gas comprising
A. a vacuum chamber;
B. pulse valve means for introducing into said chamber at a pressure of about 0.8 to 150 torr a high density pulse of sample gas, said pulse valve being connected with a source of sample gas;
C. at least one vacuum ultraviolet flashlamp positioned to direct a pulsed beam of VUV photons onto said pulse of sample gas to ionize said gas and its constituents within a spatially limited ionization region commencing at a point of exit from said valve;
D. electrostatic ion analyzer positioned adjacent said ionized gas for extraction of ions from said ionization region; and
E. detector means for detecting extracted ions external of said ionization region.

20. Apparatus as set forth in claim 19, wherein said analyzer comprises a double focus electrostatic lens.

21. Apparatus as set forth in claim 19, wherein said electrostatic analyzer comprises a symmetrical lens.

22. Apparatus as set forth in claim 20, including a stop aperture positioned in the middle of and along the axis of said electrostatic lens.

23. Apparatus as set forth in claim 19 or 21, including means for focusing said pulsed beam of VUV photons.

24. Apparatus as set forth in claim 19 or 22, whereas said pulse of sample gas has a density greater than about $2(10)^{16}$ (atoms/molecules)·cm$^{-3}$.

25. Apparatus as set forth in claim 19 or 22, including means for maintaining the vacuum in said chamber less than $10^{-3}$ torr.

26. Apparatus as set forth in claim 19 in which said detector is a mass spectrograph.

27. Apparatus as set forth in claim 19, wherein said detector means function as an ion energy analyzer.

* * * * *